United States Patent [19]

Kalidindi

[11] Patent Number: 5,471,886
[45] Date of Patent: Dec. 5, 1995

[54] UNIT-DOSE LIQUID SAMPLING DEVICE AND METHOD OF USE

[76] Inventor: Sanyasi R. Kalidindi, 8303 Hana Rd., Edison, N.J. 08817

[21] Appl. No.: 290,114

[22] Filed: Aug. 15, 1994

Related U.S. Application Data

[63] Continuation-in-part of Ser. No. 239,420, May 6, 1994, which is a continuation-in-part of Ser. No. 70,281, Jun. 2, 1993, Pat. No. 5,337,620.

[51] Int. Cl.[6] ............................................. G01N 1/12
[52] U.S. Cl. ................................................. 73/864.63
[58] Field of Search ........................ 73/863.31, 864.51, 73/864.52, 864.63, 864.64, 864.66, 864.67

[56] References Cited

U.S. PATENT DOCUMENTS

| | | | |
|---|---|---|---|
| 1,156,240 | 10/1915 | McKay | 73/864.64 |
| 1,474,807 | 11/1923 | Yetman et al. | 73/864.64 |
| 1,490,506 | 4/1924 | Buttari | 73/864.51 |
| 2,255,369 | 9/1941 | Spaeth | 73/864.63 |
| 3,242,740 | 3/1966 | Nisken | 73/864.67 |
| 3,442,017 | 5/1969 | Frenkel | 73/864.64 |
| 3,675,491 | 7/1972 | Guillet | 73/864.63 |
| 3,826,144 | 7/1974 | Wessels | 73/863.31 |
| 4,172,385 | 10/1979 | Cristensen | 73/864.63 |

FOREIGN PATENT DOCUMENTS

| | | | |
|---|---|---|---|
| 1191402 | 10/1959 | France | 73/864.63 |
| 484331 | 11/1954 | Italy | 73/864.63 |
| 0900155 | 1/1982 | U.S.S.R. | 73/864.66 |
| 702120 | 1/1954 | United Kingdom | 73/864.64 |
| 1018829 | 2/1966 | United Kingdom | 73/864.51 |
| 2032885 | 5/1980 | United Kingdom | 73/864.63 |
| 2236522 | 10/1991 | United Kingdom | 73/864.63 |

*Primary Examiner*—Robert Raevis
*Attorney, Agent, or Firm*—Richard C. Litman

[57] ABSTRACT

An extendable multiple-bottle sampling device and a method of using the device. Multiple lid holding rods nest within tubular casing segments. The casing segments have aligned bottle containers which hold unit-dose sampling bottles. These casing segments are series connected, and the device is dipped into the mixture being sampled. The last lid holding rod segment and the last tubular casing have aligned handles which are misaligned to obtain accurate volumetric sampling of pharmaceutical liquid or semi-solid mixtures, ointments, cosmetic creams and the like without wetting the outside of the sample containers.

18 Claims, 3 Drawing Sheets

UNIT-DOSE LIQUID SAMPLING DEVICE AND METHOD OF USE

CROSS-REFERENCE TO RELATED APPLICATIONS

This is a continuation-in-part application of Ser. No. 08/239,420 filed May 6, 1994, which is a continuation-in-part application of Ser. No. 08/070,281, filed Jun. 2, 1993, now U.S. Pat. No. 5,337,620.

BACKGROUND OF THE INVENTION

1. Field of the Invention

The present invention relates to a sampling device or tool useful in taking precise sample volumes of liquid or emulsion mixtures at various depths simultaneously by utilizing sample bottles having varying sample volumes encased in lidded containers spaced at regular intervals on a tubular sampling device. This device enables the procurement of these samples from even large blenders or containers by providing a segmented sampler design.

2. Description of the Prior Art

In the manufacture of liquid unit-dosage form pharmaceutical or cosmetic mixtures, one of the critical processing steps is the blending of the active ingredient(s) with the inactive ingredient(s) in a blender or mixer. Before further processing of such mixtures, samples are taken from different areas of these mixtures and analyzed to check whether or not the active ingredient is uniformly distributed. Such a test is called a content uniformity test or a homogeneity test. Whenever a liquid or a semi-solid mixture is tested for homogeneity, the test results would be influenced by the sample size and the sampling technique. In order to insure accurate testing, the sample size should be as close to the unit dose as possible, and the sampling technique should be such that the mixture is minimally disturbed during sampling. However, unit-dose sampling of mixtures with varying dosages and bulk densities requires multiple sampling devices. The other factors that compound this problem are the large range of mixer sizes, limited clearance between the top of the mixer and the ceiling, the necessity of taking multiple samples, the requirement of thorough cleanability of the device, and the necessity of preventing contamination of samples by minimizing the danger of losing loose device parts such as hinges and fasteners in the mixture. All these factors together impose an economic penalty on the manufacturer.

The present invention overcomes these problems by providing a sampling device that permits the following advantages. (1) Unit-dose sampling is accomplished at various depths of the mixture by using bottles of varying volumes. (2) The sampling location in the mixture is readily changed by the use of blocked adapters or bottle containers to block any of the sampling locations. (3) The outside surface of the sampling bottles is kept dry which enhances subsequent handling. (4) Large blenders/mixers are readily sampled by utilizing the multiple lid holding rod and the outer casing in sections that are joined above or within the blender/mixer. (5) Thorough cleaning of the outer casing is enabled by utilizing a sampling device with an open bottom. (6) There are no loose moving parts on the inventive device.

A number of patents have been issued that address sampling of various materials. These patents will be discussed in the order of their perceived relevance to the claimed invention.

In Italian Patent No. 484,331 issued in November, 1954 to Dino Donadon, there is disclosed a sampler of immiscible liquids which consists of an inner tube containing partitioned volumes with apertures for each compartment, an outermost tube, and an intermediate tube with apertures which align with both the inner tube's apertures and corresponding apertures in the outermost tube. A portion of the second tube's apertures contains a filter. The innermost tube and the intermediate tube have separate handles for alignment of their respective apertures with the apertures of the outer tube in order to take samples of an immiscible liquid system. There is no disclosure of multiple sampling by external containers with a common lid system, segmentation of the sampler, an open tip, and the operation of his sampler without the essential intermediate tube and associated filters.

In the British Patent Application No. 2,032,885 published on May 14, 1980 to John R. Bennett, a liquid sampling apparatus is disclosed having a removable sampling vessel positioned on an elongated backbone with a fixed lid attached to a separate handle rod aligned with the backbone to take a liquid sample without lateral movement of the lid. There is no disclosure of multiple sampling capability or segmentation of the apparatus. There is no apparent need to keep the outside of the bottle free of the coal flotation liquid and coal particles.

In U.S. Pat. No. 3,675,491 issued on Jul. 11, 1972 to Phillippe R. Guillet, there is disclosed a liquid or powder sampler device with a simple rod inside a tube with opens a spring biased lid for the sampling container. Again, there is no suggestion of the use of multiple sampling, segmentation of the device and protection from contamination of the outside of the sampling container.

In U.S. Pat. No. 1,156,240 issued on Oct. 12, 1915 to George L. McKay, a milk sampler is disclosed which utilizes three elements including an apertured tube within another apertured outer tube with two slots in each tube. The third element is a liquid expelling piston means. There is no suggestion of multiple sampling or use of separate containers.

In U.S. Pat. No. 2,255,369 issued on Sep. 9, 1941 to Charles Spaeth and a British patent application Ser. No. 2,236,522 A published on Oct. 4, 1991 to Riginos Kimonides, individual container liquid samplers are disclosed involving elaborate container opening mechanisms.

In U.S. Pat. No. 1,474,807 issued on Nov. 20, 1923 to Oscar B. Yetman et al. and in U.S. Pat. No. 3,442,017 issued on May 6, 1969 to Francis Frenkel, there are disclosed liquid samplers having multiple compartments. There is no suggestion for external containers or segmentation of the sampling devices.

Finally, in British Patent Specification Serial No. 702,120 published on Apr. 28, 1987 to the United Africa Company Limited and in French Patent No. 1,191,402 issued on Oct. 20, 1959 to Raphael J. R. Moreau, apertured tubes within apertured tubes with handles but uncompartmentalized sampling are disclosed.

The disclosures and the prior art discussed in the above related applications are hereby incorporated by reference herein.

None of the above inventions and patents, taken either singly or in combination, is seen to describe the instant invention as claimed.

SUMMARY OF THE INVENTION

The present invention is a multiple-sample, segmented sampling device or tool and a method for utilizing said device for obtaining multiple bottle samples of precise and selectively variable volumes from different levels in a blender or mixer containing pharmaceutical liquids, ointments, creams or other semi-solid emulsions in one sampling attempt. Sampling bottles having varying specific volumes are placed within lidded containers mounted on a tubular rod of a predetermined length. The lids are mounted on a separate rod contained within the tubular rod so that the bottles are opened for sampling and closed after sampling at simultaneously. The lids may have vacuum pulling means via the hollow lid holder rod to enhance the filling of smaller bottles with thicker viscosity liquids.

Accordingly, it is a principal object of the invention to provide a sampling device or tool and a method for its use wherein samples of varying volumes may be obtained from several depths of liquid or semi-liquid material.

It is another object of the invention to provide a sampling device with one or more blocked sampling containers in order to change the depth of sampling or to reduce the number of samples.

It is an object of the invention to provide adapters within the containers to support sampling bottles of different capacities.

It is a further object of the invention to provide connection means between the receiving rod segments and between the tubular casing segments.

Still another object of the invention is to provide terminal apparatus such as suction means at the distal end of the sampling device to enable complete filling of smaller bottles.

Another object of the invention is to provide positioning means for the handle in the last tubular casing's proximate end to rotate the lids to expose the mouths of the sampling bottles.

It is a yet another object of the invention to fabricate the device from stainless steel and/or plastic materials.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
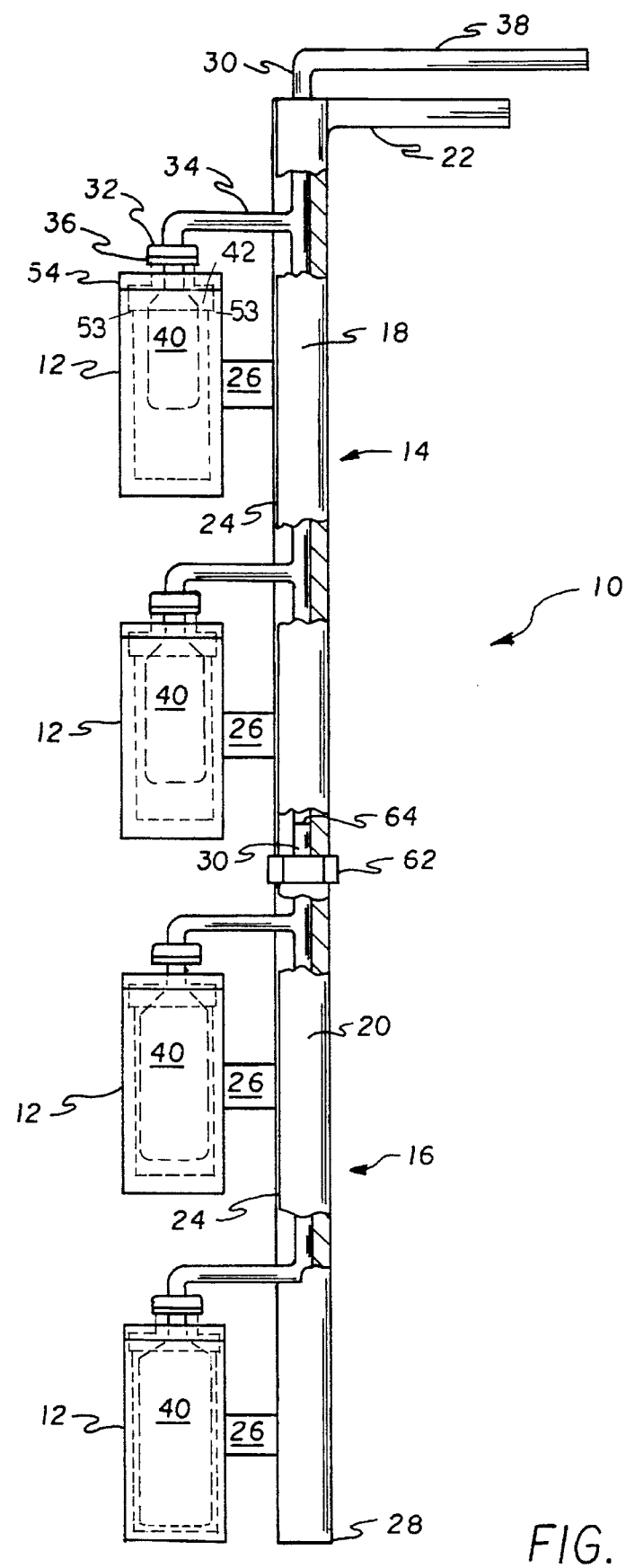
FIG. 1 is a side elevational view with partial breakaway views of the preferred embodiment of the segmented sampling device utilizing solid lid holding rods cooperating with the slot in the tubular casing which has at least two sampling containers per segment.

Referring to FIG. 1, the preferred embodiment of the sampling device is shown. The liquid sampling device 10 has a plurality of bottle containers 12 arranged in linear formation, one directly below the other, with two containers per segment 14 and 16. Upper segment 14 consists of outer casing 18, handle 22, slot 24 for positioning the lids 32, and wedges 26 connecting containers 12 to the casing 18. The segments 14 and 16 are joined by union nut 62. The lower casing 20 has an open bottom 28 for cleaning accessibility, and the slot 24 extends only to the top of the lowermost bottle container 12. The lid holding rod 30 is a solid rod in this embodiment and holds lids 32 by connecting arms 34. In the segmented embodiment, rods 30 are connected by otherwise conventional socket connectors (not shown but disclosed in the art incorporated by reference herein) wherein the joint is shown by line 64. Lids 32 have flexible sealing pads 36 preferably made from neoprene.

Figure 2:
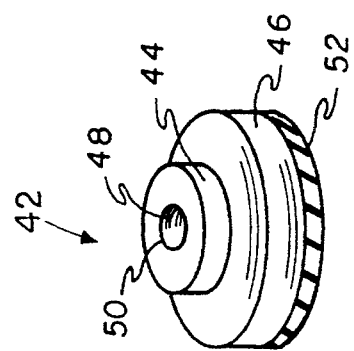
FIG. 2 is an isometric view of the adapter lid which has different sized threaded holes adapted to secure the mouths of different sized bottles.
Figure 3:
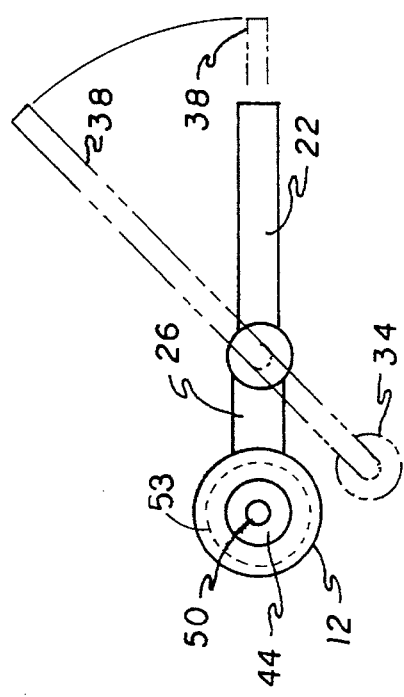
FIG. 3 is a top plan view of the liquid sampler showing the position of the lids rotated away from the sampling containers.

Sample bottles 40 of various capacities are held securely inside the containers 12 by adapters 42 shown in detail in FIG. 2. The plastic adapters 42 consist of a neck 44 with female threading 48 protruding from base 46 to cooperate with the threaded neck of bottle 40. The aperture 50 will of necessity vary in size to correspond with the neck sizes of the sampling bottles 40. Adapter 42 has a seal 52, preferably made of neoprene, which insures prevention of liquid being sampled from entering the bottle container 12 in the space between the sampling bottle 40 and the bottle container 12. Adapter neck 44 must fit snugly within the hole in cap 54 of container 12. The adapter base 46 and seal 52 rest on an edge 53 formed inside the container 12 situated below the threading (shown in FIGS. 1 and 3) of the cap 54 being screw threaded onto container 12. This structure prevents the outside surface of the sampling bottle within the bottle container 12 from becoming wet with the sampled liquid.

Figure 4:
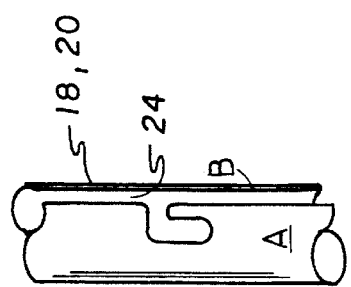
FIG. 4 is a partial frontal view of the slot in the outer casing in which the arms supporting the lids are positioned.

Although FIG. 1 depicts the neck of the sampling bottle 40 being exposed, it should be made clear that the bottle mouth could be flush with the top surface of cap 54. In the top plan view of FIG. 3, the positions of the lids 32 removed from the bottle containers 12 are illustrated when rod handle 38 is rotated approximately 45 degrees. In FIG. 4, one of the intermediate slots 24 in outer casing 18 or 20 is depicted to illustrate the position A wherein the lids 34 have covered the open bottles 40 and position B wherein the bottles are unlidded.

Figure 5:
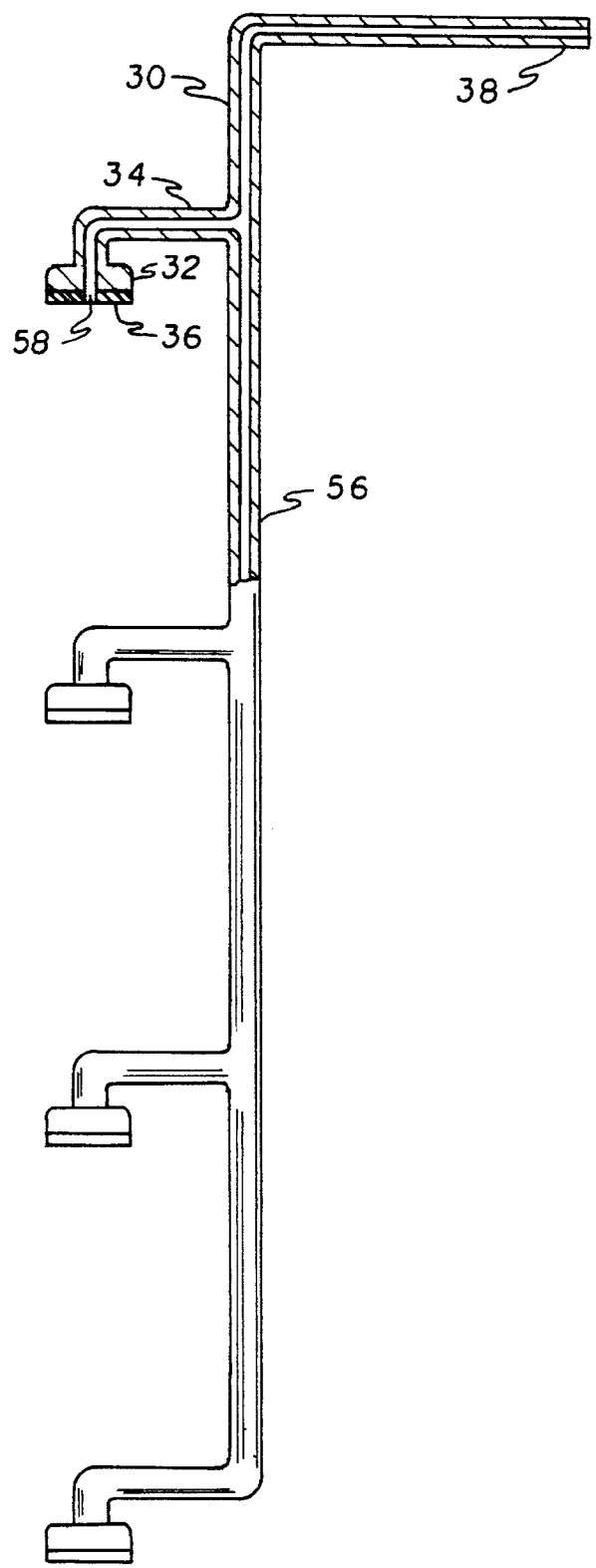
FIG. 5 is a partial elevational view and cross-sectional view of a second embodiment of a hollow holding rod for the lids enabling the application of a vacuum from the handle.

Turning now to the second embodiment of FIG. 5, wherein a modification of the lid-holding rod is illustrated to show a hollow rod 56 including apertures 58 in the lids 34 and seals 36. Filling of small bottles is improved by utilizing this hollow rod with application of a vacuum from the handle 38 prior to but not during sampling. Appropriate valve means (not shown) may be present in the handle 56 to maintain a vacuum after the vacuum source has been disconnected.

The sampling process begins with the selection of bottle sizes for each bottle container 12 with the properly fitting adapter 42. The lids 32 are positioned over the bottle openings in one maneuver. Hand pressure over handles 22 and 38 ensures closure of each sampling bottle while the sampling device 10 is lowered into position in the liquid mixture being blended. FIG. 4 shows this step in the process with the arm 34 (not shown) resting in the lowest position A in groove 24 of tubular casings 18, 20. Upon rotating the lid holding rod handle 38 approximately 45 degrees, the lids 32 are moved away from each container 12 and the sampling bottles 40 are filled. Then the rod handle 38 is rotated back to cover all the bottles in unison. If no sample is desired at any position, a closed bottle 40 or adapter 42 may be inserted in container 12 at that position. It may be desirable to fill the bottle 40 and the container 12 with a liquid in order to negate buoyancy of the device.

The device 10 may consist in the main of stainless steel except for the plastic adapter 42 and neoprene seals 36 and 52. The adapter 42 may be made from commercially available plastic such as TEFLON (®), or an acetal polymer resin, commercially available as DELRIN (®). The bottles may be composed of high density polyethylene and may vary in volume from 1 c.c. to 1 liter. The containers 12 may be spaced at one foot intervals. The total length of device 10 may be as long as 15 feet.

Retrieval of a long sampling device according to the present invention from the sampling area may be accomplished according to the room available above the mixing vessel. If there is adequate room, no dismantling would be necessary. Dismantling may be performed in disengaging several connected segments at a time.

The second embodiment involves the use of a hollow lid holding rod 56 depicted in FIG. 5. When small sampling bottles are utilized, it has been found that air within these bottles prevent complete filling. Therefore, the application of a vacuum from the rod handle 68 until the opening of the bottles to the liquid medium has solved the aforementioned problem of incomplete filling.

In summary, the objectives of obtaining accurate volumetric samples at different depths and in the same time period are obtained by the use of this sampling device as well as the facility of obtaining different liquid volumes in the same device. The outside surface of the sample bottles utilized are substantially free of the liquid being sampled.

It is to be understood that the present invention is not limited to the embodiments described above, but encompasses any and all embodiments within the scope of the following claims.

I claim:

1. A multiple-sample sampling device capable of extension for taking multiple samples having accurate volumes at different depths of liquids or semi-solid mixtures, comprising:

at least one tubular casing segment of predetermined length comprising, a slot extending from its proximate end to either its distal end or proximate its distal end, a plurality of bottle containers appended to said at least one tubular casing segment, and a handle at-its proximate end;

each bottle container including an apertured cover, an apertured adapter positioned within said cover and a container body;

at least one rod element means with a handle which fits inside said at least one tubular casing segment, and having multiple arms positioned perpendicularly to said at least one rod element means and ending in a right angle bend;

each arm supporting a lid at said end; and an empty bottle secured within each bottle container by said adapter;

whereby, said each empty bottle receives a full unit-dose sample of said liquid mixture by removing each said lid simultaneously when said lid holding rod handle is rotated, and terminating the sampling by rotating back each said lid to simultaneously cover each filled bottle.

2. The sampling device according to claim 1, comprising at least two segments of tubular casing with appended bottle containers and containing lid holding rods which are connectable in series, thereby extending the length of the sampling device.

3. The sampling device according to claim 1, comprising at least one solid lid holding rod segment.

4. The sampling device according to claim 1, comprising at least one hollow lid holding rod segment, whereby a vacuum can be applied on said open sampling bottles.

5. The sampling device according to claim 1, comprising an adapter means contained in said bottle container to secure bottles having various sizes.

6. The sampling device according to claim 5, wherein said adapter means is fabricated of plastic with a neoprene sealer bottom.

7. The sampling device according to claim 1, wherein said tubular casing and lid holding rod are made of stainless steel.

8. The sampling device according to claim 1, wherein said bottles are fabricated of high density polyethylene.

9. The sampling device according to claim 1, wherein each said lid has a neoprene bottom.

10. The sampling device according to claim 1, wherein at least two solid lid holding rods are connected by a socket connection.

11. The sampling device according to claim 1, wherein at least two tubular casing segments are secured by a union nut.

12. A method of sampling a liquid pharmaceutical or cosmetic mixture by the use of a segmented sampling device, comprising:

positioning into a liquid pharmaceutical or cosmetic mixture a first sampling device segment comprising a first tubular casing segment open at its distal end, with appended and aligned sample bottle containers containing empty sample bottles of varying sizes, and a first tubular casing segment containing a multiple lid holding rod, wherein the open sample bottles are closed by the lids;

attaching a last segment having handles for both a last lid holder and a last tubular casing;

turning the handle of the last lid holder rod to rotate the lids away from the open sample bottles to obtain precise sample volumes of said liquid; and returning the handle to its original position to close off the open sample bottles with the lids.

13. The method of claim 12, comprising the use of solid lid holder rod segments.

14. The method of claim 13, comprising the step of placing at least one blocked adapter in an empty bottle container to prevent sampling of at least one liquid level.

15. The method of claim 12, comprising the use of hollow lid holder rod segments, whereby application of a vacuum from the handle ensures complete filling of said sample bottles.

16. The method of claim 12, comprising the step of placing sample bottles varying from 1 c.c. to 1 liter in volume in the bottle containers.

17. The method of claim 12, comprising the step of providing at least one blocked and liquid filled bottle to prevent sampling of at least one liquid level.

18. In a process of taking precise volumetric samples from a liquid containing mixture at varying depths simultaneously, the improved process comprising the steps of:

inserting at least one tubular casing segment of predetermined length into the liquid containing mixture, wherein the casing segment comprises a slot extending from its proximate end to either its distal end or proximate its distal end, and multiple bottle containers with sampling bottles of varying unit-dose volumes contained therein are appended to said casing segment, each bottle container made up of an apertured cover, an apertured adapter positioned within said cover and a container body;

at least one lid holding rod having multiple lids positioned on perpendicular arms being inserted in said at least one tubular casing segment;

at least one additional sampler segment comprising another lid holding rod and another tubular casing with bottle-containing containers being added;

a last segment made up of the tubular casing with a first handle and the lid holding rod with a second handle, the unit-dose sampler taking samples by displacing said lid holding rod handle relative to the tubular casing handle to expose and fill the sampling bottles simultaneously with the liquid contain mixture being sampled; and returning the displaced lid holding rod handle to its original position to complete the sampling.

* * * * *